(12) United States Patent
Sim

(10) Patent No.: US 11,320,426 B2
(45) Date of Patent: May 3, 2022

(54) BIOSENSOR FOR DIAGNOSING ALZHEIMER'S DISEASE USING RAYLEIGH SCATTERING AND COLORIMETRIC ASSAY OF GOLD NANOPARTICLE AND MULTI-DETECTION METHOD USING THE BIOSENSOR

(71) Applicant: PHARMAWORKS CO., LTD., Seoul (KR)

(72) Inventor: SangJun Sim, Seoul (KR)

(73) Assignee: PHARMAWORKS CO., LTD., Seoul (KR)

( * ) Notice: Subject to any disclaimer, the term of this patent is extended or adjusted under 35 U.S.C. 154(b) by 0 days.

(21) Appl. No.: 16/686,610

(22) Filed: Nov. 18, 2019

(65) Prior Publication Data

US 2020/0124596 A1 Apr. 23, 2020

Related U.S. Application Data

(63) Continuation-in-part of application No. 15/971,688, filed on May 4, 2018, now abandoned.

(51) Int. Cl.

| | | |
|---|---|---|
| *G01N 33/543* | (2006.01) | |
| *G01N 33/531* | (2006.01) | |
| *G01N 33/68* | (2006.01) | |
| *G01N 21/25* | (2006.01) | |
| *B82Y 5/00* | (2011.01) | |
| *B82Y 15/00* | (2011.01) | |

(52) U.S. Cl.
CPC ....... *G01N 33/54346* (2013.01); *G01N 21/25* (2013.01); *G01N 33/531* (2013.01); *G01N 33/54393* (2013.01); *G01N 33/6896* (2013.01); *B82Y 5/00* (2013.01); *B82Y 15/00* (2013.01); *G01N 2021/258* (2013.01); *G01N 2800/2821* (2013.01)

(58) Field of Classification Search
None
See application file for complete search history.

(56) References Cited

U.S. PATENT DOCUMENTS

| | | |
|---|---|---|
| 2011/0014724 A1 | 1/2011 | Sim et al. |
| 2018/0238908 A1 | 8/2018 | Nithiyanandam |

FOREIGN PATENT DOCUMENTS

KR    10-1003124 B1    12/2010

OTHER PUBLICATIONS

Gao "Ab40 Oligomers Identified as a Potential Biomarker for the Diagnosis of Alzheimer's Disease" PLOS1 5(12):e15725 (7 pages) (Year: 2010).*
Baller, M. K., et al. "A Cantilever Array-Based Artificial Nose." *Ultramicroscopy* 82.1-4 (2000): 1-9. (9 pages, in English).
Marx, Kenneth A. "Quartz Crystal Microbalance: A Useful Tool For Studying Thin Polymer Films And Complex Biomolecular Systems At The Solution—Surface Interface." *Biomacromolecules* 4.5 (2003): 1099-1120. (22 pages, in English).
Yuqing, Miao, et al. "Ion Sensitive Field Effect Transducer-Based Biosensors." *Biotechnology Advances* 21.6 (2003): 527-534. (8 pages, in English).
Hanrahan, Grady, et al. "Electrochemical Sensors For Environmental Monitoring: Design, Development And Applications." *Journal of Environmental Monitoring* 6.8 (2004): 657-664. (8 pages, in English).
Han, Sang Hee, et al. "Detection Of Mutant P53 Using Field-Effect Transistor Biosensor." *Analytica Chimica Acta* 665.1 (2010): 79-83. (5 pages, in English).
Zhou, Wei, et al. "A Label-Free Biosensor Based On Silver Nanoparticles Array For Clinical Detection Of Serum P53 In Head And Neck Squamous Cell Carcinoma." *International Journal Of Nanomedicine* 6 (2011): 381-386. (7 pages, in English).
Duan, R. Q., et al., "Detection Of P53 Gene Mutation By Using A Novel Biosensor Based On Localized Surface Plasmon Resonance." *Neoplasma*, 59.3 (2012): 348-353. (6 pages, in English).
Shah, Nilay S., et al., "Midlife Blood Pressure, Plasma βAmyloid, and the Risk for Alzheimer Disease: the Honolulu Asia Aging Study", *Hypertension* vol. 59, No. 4, Mar. 5, 2012 (pp. 780-786).
Pekeles, Heather, et al., "Development and validation of a salivary tau biomarker in Alzheimer's disease." *Alzheimer's & Dementia: Diagnosis, Assessment & Disease Monitoring*, vol. 11, Apr. 19, 2018 (pp. 53-60).

* cited by examiner

*Primary Examiner* — Adam Weidner
(74) *Attorney, Agent, or Firm* — NSIP Law

(57) ABSTRACT

The present invention relates to a nanoplasmonic sensor based on gold nanoparticle to which an antibody or an aptamer binds, the antibody or the aptamer recognizing Aβ 1-40, Aβ 1-42, and τ protein, which are Alzheimer's disease onset markers that are present in blood, and a multi-detection method of Alzheimer's disease using Rayleigh scattering phenomenon and colorimetric assay of the sensor. The present invention has advantages in that it is possible to perform simultaneous multiple detect with respect to various onset markers by using a simple diagnosis method using blood, and sensitivity of diagnosis is improved by using a chaotropic solvent.

1 Claim, 20 Drawing Sheets

【Figure 1】
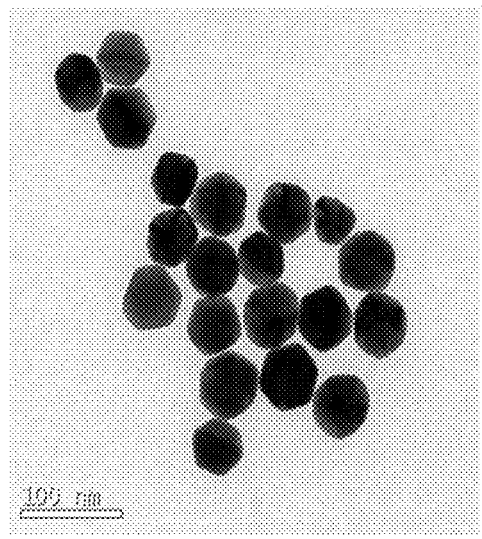
【Figure 2】
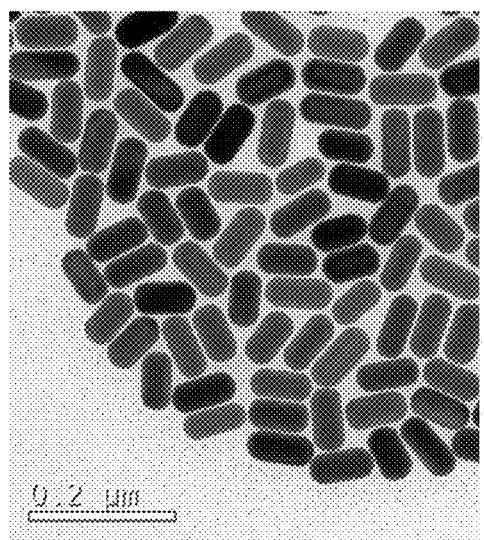

[Figure 9]
[Figure 10]
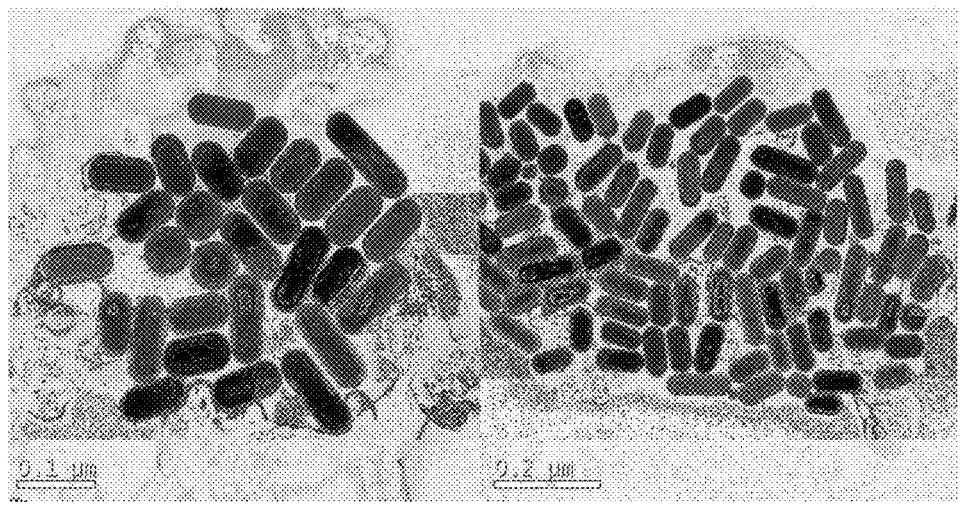

[Figure 11]
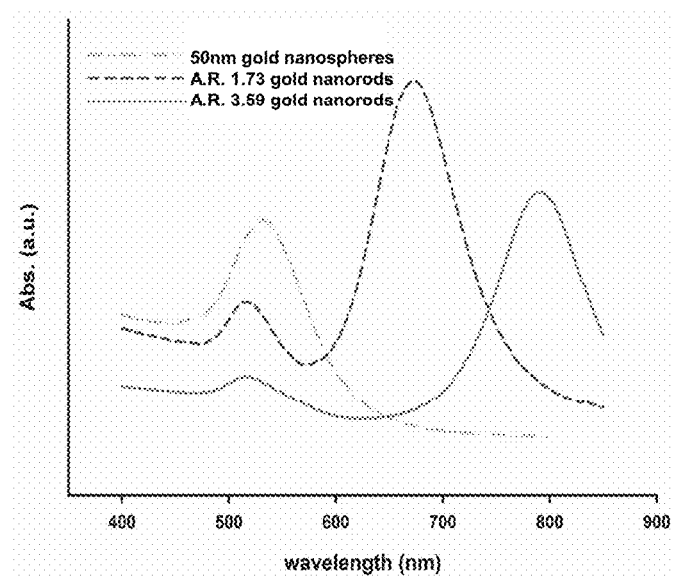
[Figure 12]
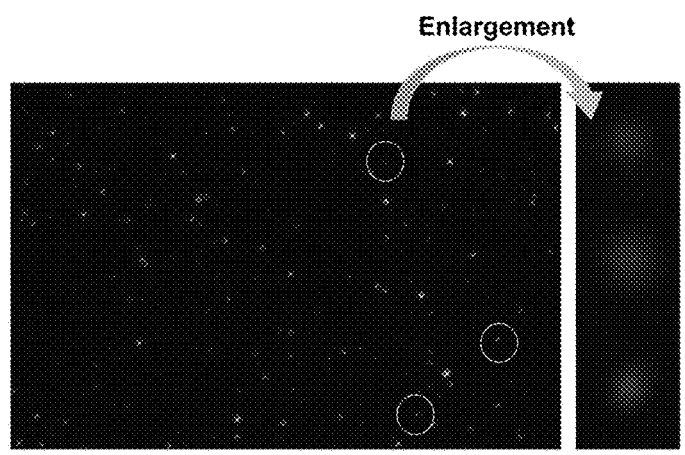

[Figure 13]
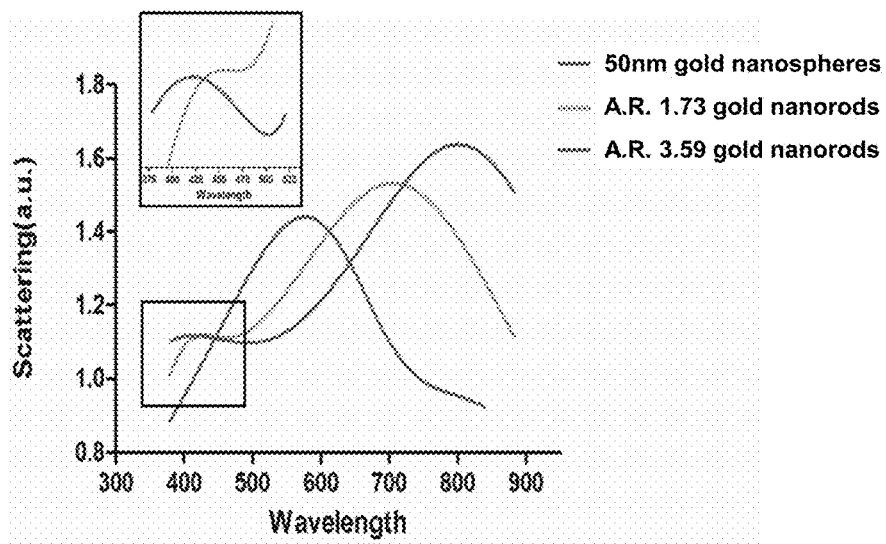
[Figure 14]
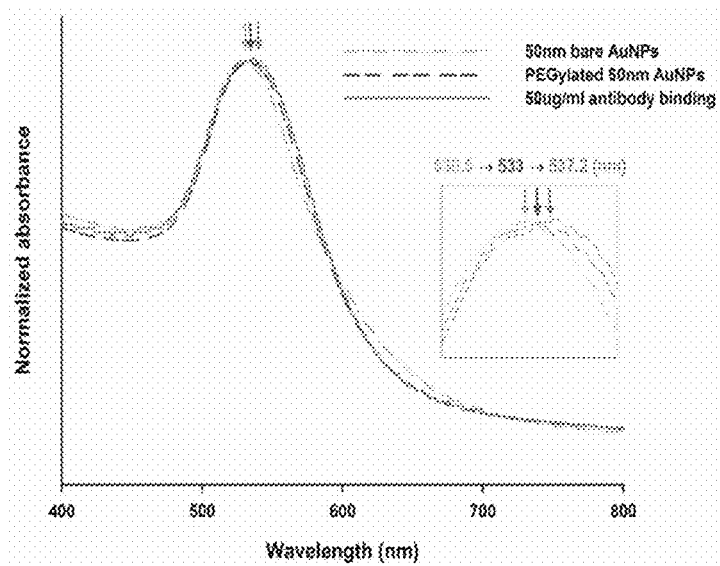

[Figure 22]
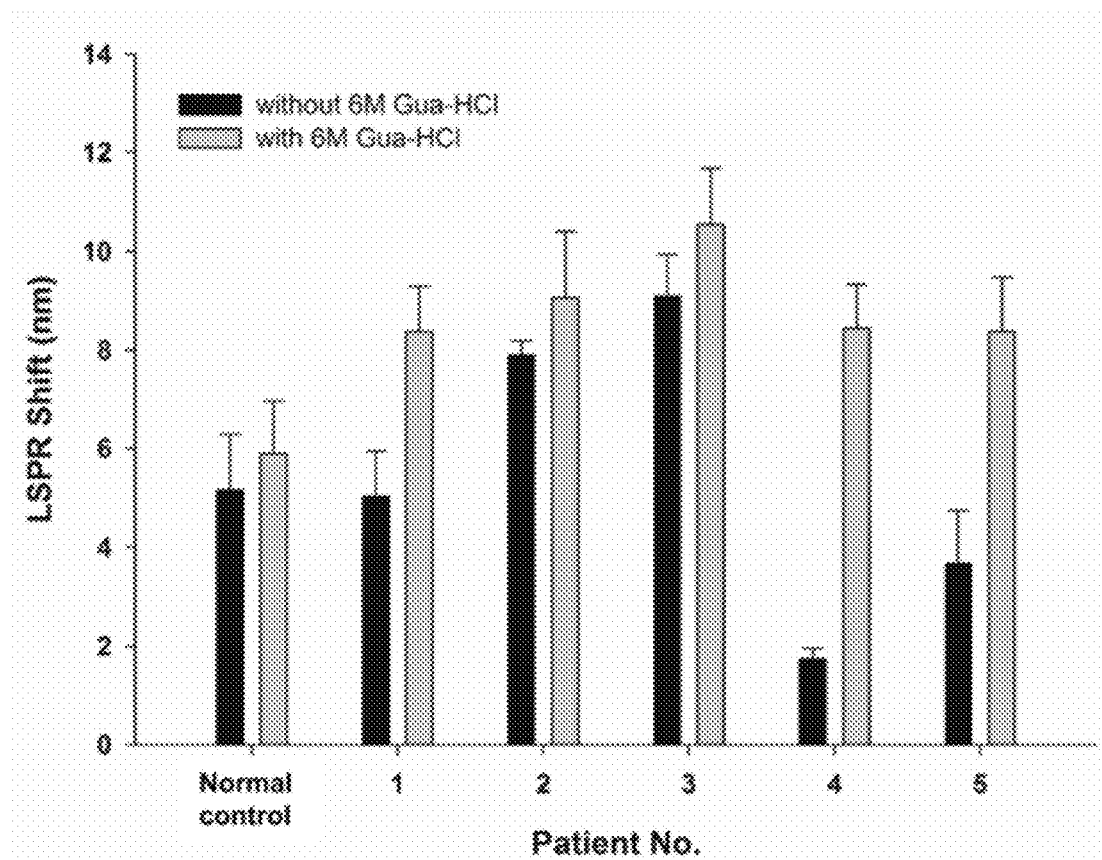

BIOSENSOR FOR DIAGNOSING ALZHEIMER'S DISEASE USING RAYLEIGH SCATTERING AND COLORIMETRIC ASSAY OF GOLD NANOPARTICLE AND MULTI-DETECTION METHOD USING THE BIOSENSOR

CROSS-REFERENCE TO RELATED APPLICATIONS

This application is a continuation in part of U.S. patent application Ser. No. 15/971,688 filed on May 4, 2018, the entire disclosure of which is incorporated herein by reference for all purposes.

TECHNICAL FIELD

The present invention relates to a biosensor for diagnosing Alzheimer's disease using Rayleigh scattering and colorimetric assay of a gold nanoparticle and a multi-detection method using the biosensor, and more particularly, to a nanoplasmonic sensor recognizing Aβ 1-40, Aβ 1-42, and τ protein, which are Alzheimer's disease onset markers that are present in blood, and a multi-detection method of Alzheimer's disease using the sensor.

BACKGROUND ART

Alzheimer's disease has histological features of amyloid plaque and neurofibrillar tangle at the hippocampus and cortex, and is a degenerative disease that weakens social function of a patient by exacerbating cognitive disorder affecting the patient's memory. Alzheimer's disease is a type of disease that has slow a disease progression rate, but the disease progresses above a certain level is not able to be remissible, and thus early diagnosis is very important. To date, diagnostic methods include brain imaging, cognitive testing, and examination through cerebrospinal fluid, etc. However, these methods are applicable only after symptoms of Alzheimer's disease are manifested, which is insufficient for early diagnosis. In addition, a lot of economic cost for diagnosis is required, and it is accompanied by an operative method, and thus the risk is very high. Therefore, it is important to develop a simple method for early diagnosis of Alzheimer's disease, and thus, there is an urgent need to develop a highly sensitive diagnostic method for detecting a trace amount of onset biomarker present in blood.

Currently, a material that is considered as the most important indicator as a causative agent in pathogenesis of Alzheimer's disease includes Aβ 1-40, Aβ 1-42 peptide, and τ protein, etc.

The beta-amyloid peptide is produced by cleaving an amyloid precursor protein by beta-secretase and gamma-secretase. Thus, as activity of these enzymes increases, the production of beta-amyloid peptide increases, which is closely related to Alzheimer's disease. However, if the alpha-secretase which cleaves an intermediate region of the beta-amyloid peptide increases its activity, the production of beta-amyloid peptide rather decreases. Alpha-secretase predominates in normal subjects and prevents amyloid beta cleavage by beta-secretase. When these beta-amyloid peptides accumulate in the brain, large amounts of reactive oxygen are produced, causing oxidative damage and causing death of nerve cells. In addition, beta-amyloid peptide causes excessive accumulation of intracellular calcium, causing cell death due to excitotoxicity. The death of nerve cells due to the beta-amyloid peptides, particularly, cell death in hippocampus, a region associated with memory, induces memory loss, which is a typical symptom of dementia. A major plaque component of beta-amylase produced by sequential cleavage by the secretase is known as isoform of Aβ 1-42 peptide involved in formation of neurotoxic oligomer and plaque formation in an onset mechanism of Alzheimer's disease.

Recently, it has been reported that in addition to beta-amyloid, τ protein has an abnormal structure and forms an inclusion body, which causes degenerative brain disease. It is known that the τ protein is necessary to stabilize microtubules like a connecting steel of a railroad. As the τ protein accumulates excessively, the microtubules collapse and a network of normal nerve cells breaks down. A cause of accumulation of the τ protein is that phosphorus is excessively attached to the τ protein to form a polymer due to phosphorylation, and a disease caused by accumulation of the τ protein and aggregation of nerve cells is called Topathy and has been indicated as a cause of various degenerative brain diseases.

Meanwhile, recently, biosensor technology has focused on development of non-labeling measurement technology that does not use a labeling material, and typically includes a method of using a surface plasmon resonance phenomenon occurring on a metal surface (R. Q. DUAN et al., Neoplasma, 59(3):348, 2012; Wei Zhou et al., International Journal of Nanomedicine, 6:381, 2011), a method of measuring a change in refractive index of light due to bending phenomenon of a cantilever which is a three-dimensional microstructure (Balle, M K. et al., Ultramicroscopy, 82; 1, 2000), a method of measuring a change in resonance frequency of crystals according to a change in mass of biomolecules (Marx, K A., Biomacromolecules, 4; 1099, 2003), a method of measuring an electric field effects based on semiconductor process (Yuqing, M. et al., Biotechnol. Adv., 21; 527, 2003), and an electrochemical measurement method (Hanahan, G. et al., J. Environ. Monit., 6; 657, 2004; Sang Hee Han et al., Analytica Chimica Acta, 665:79, 2010), etc.

Among them, the localized surface plasmon resonance (LSPR) method is able to quantitatively detect a reaction without complicated pre-purification and labeling processes, and thus it has been used in a number of studies on interaction between biomolecules immobilized on a surface. In the LSPR method, when light having various wavelengths is irradiated to a material having a localized surface such as a metal nanoparticle, unlike a bulk metal, polarization is generated on a surface of the metal nanoparticle, and a peculiar characteristic that intensity of the electric field is increased is shown. LSPR optical property is sensitive to a change in dielectric constant (refractive index) generated near the nanoparticle. This change in dielectric constant (refractive index) may be used to detect adsorption between biomolecules. For the past several decades, various biomolecule interaction analyses have been performed based on the optical properties of the LSPR to measure biomaterial concentration, thickness, and binding reaction rate data for a particular biochemical analyte, including antigen/antibody, ligand/receptor, protein/protein reaction, and DNA hybridization.

Therefore, the present inventors have made intensive efforts to develop a novel multiple detection platform capable of early diagnosis of Alzheimer's disease, and as a result, confirmed that Aβ 1-40, Aβ 1-42, and τ protein, which are three markers of Alzheimer's disease onset that are present in blood, could be detected using a nanoplasmonic sensor, and completed the present invention.

RELATED ART DOCUMENT (Patent Document 1) Korean Patent No. 10-1003124

DISCLOSURE

Technical Problem

An object of the present invention is to provide a method for diagnosing Alzheimer's disease using Rayleigh scattering and colorimetric assay of a plasmonic sensor based on a gold nanoparticle to which an antibody is immobilized, and a biosensor for diagnosing Alzheimer's disease.

Technical Solution

In order to achieve the foregoing objects, the present invention provides a method for diagnosing Alzheimer's disease comprising (A) contacting a sample separated from a specimen with a plasmonic sensor based on a gold nanoparticle to which an antibody or an aptamer specific to a target protein of which expression is specifically increased or decreased in Alzheimer's patient is immobilized, thereby inducing a binding between the target protein and the antibody or the aptamer; (B) measuring light scattering spectrum according to the binding; and (C) determining whether or not Alzheimer's disease occurs through analysis of maximum wavelength mobility (Amax) obtained from the spectrum.

The present invention also provides a biosensor for detecting Alzheimer's disease in which an antibody or an aptamer of at least one target protein selected from the group consisting of Aβ 1-40 peptide, Aβ 1-42 peptide, and T protein is immobilized to a gold nanoparticle.

DESCRIPTION OF DRAWINGS

The patent or application file contains at least one drawing executed in color. Copies of this patent or patent application publication with color drawing(s) will be provided by the Office upon request and payment of the necessary fee.

FIG. 1 shows an HR-TEM image of a 50 nm-sized circular gold nanoparticle produced in Example 1-1.

FIG. 2 shows an HR-TEM image of a rod-shaped gold nanoparticle having an aspect ratio of 1.73 and produced in Example 1-2.

FIG. 9 shows a dark field image of the rod-shaped gold nanoparticle having an aspect ratio of 3.59 produced in Example 1-3 exposed at 1000 times magnification.

FIG. 10 shows an HR-TEM image of a mixture in which the 50 nm-sized circular gold nanoparticle, the rod-shaped gold nanoparticle having an aspect ratio of 1.73, and the rod-shaped gold nanoparticle having an aspect ratio of 3.59 are mixed.

FIG. 11 shows UV-Vis spectrum of the mixture in which the 50 nm-sized circular gold nanoparticle, the rod-shaped gold nanoparticle having an aspect ratio of 1.73, and the rod-shaped gold nanoparticle having an aspect ratio of 3.59 are mixed.

FIG. 12 shows a dark field image of a mixture in which the 50 nm-sized circular gold nanoparticle, the rod-shaped gold nanoparticle having an aspect ratio of 1.73, and the rod-shaped gold nanoparticle having an aspect ratio of 3.59 are mixed.

FIG. 13 shows localized surface plasmonic resonance spectrum of the mixture in which the 50 nm-sized circular gold nanoparticle, the rod-shaped gold nanoparticle having an aspect ratio of 1.73, and the rod-shaped gold nanoparticle having an aspect ratio of 3.59 are mixed.

FIG. 14 shows UV-Vis change spectrum shown for each step in binding PEG and an antibody to the circular gold nanoparticle.

FIG. 22 shows LSPR $\lambda_{max}$ shifts of nanoplasmonic biosensor for detecting τ protein in cognitive normal control and AD patients' blood samples (Patient No. 1-5) combined with 6M Gua-HCl.

BEST MODE

Figure 3:
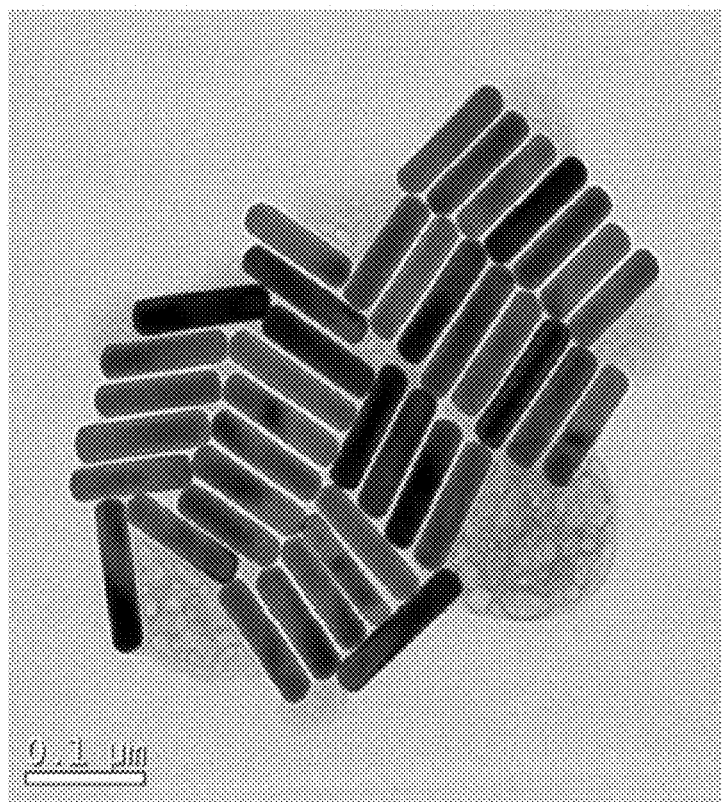
FIG. 3 shows an HR-TEM image of a rod-shaped gold nanoparticle having an aspect ratio of 3.59 and produced in Example 1-3.
Figure 4:
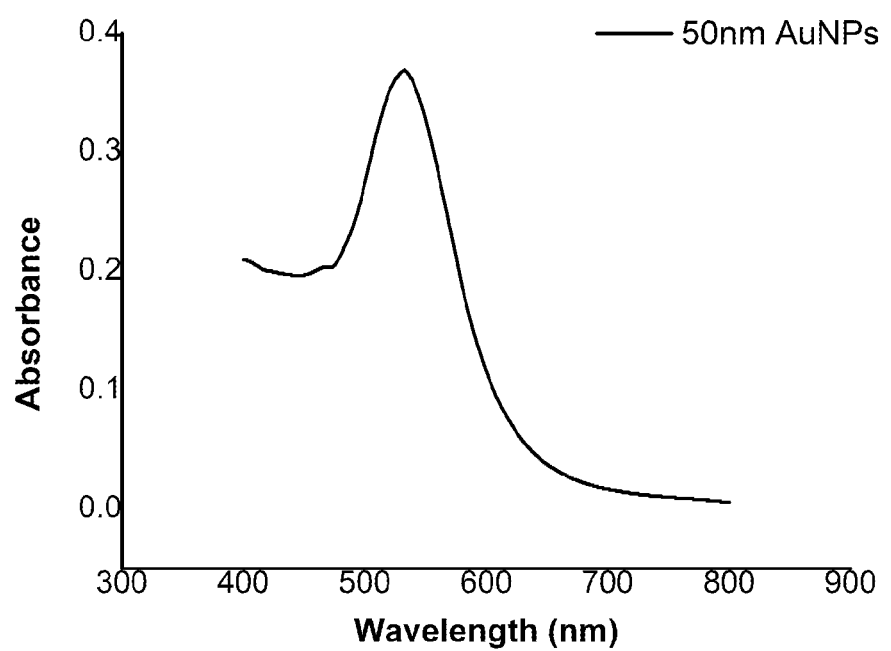
FIG. 4 shows UV-Vis spectrum of the 50 nm-sized circular gold nanoparticle produced in Example 1-1.
Figure 5:
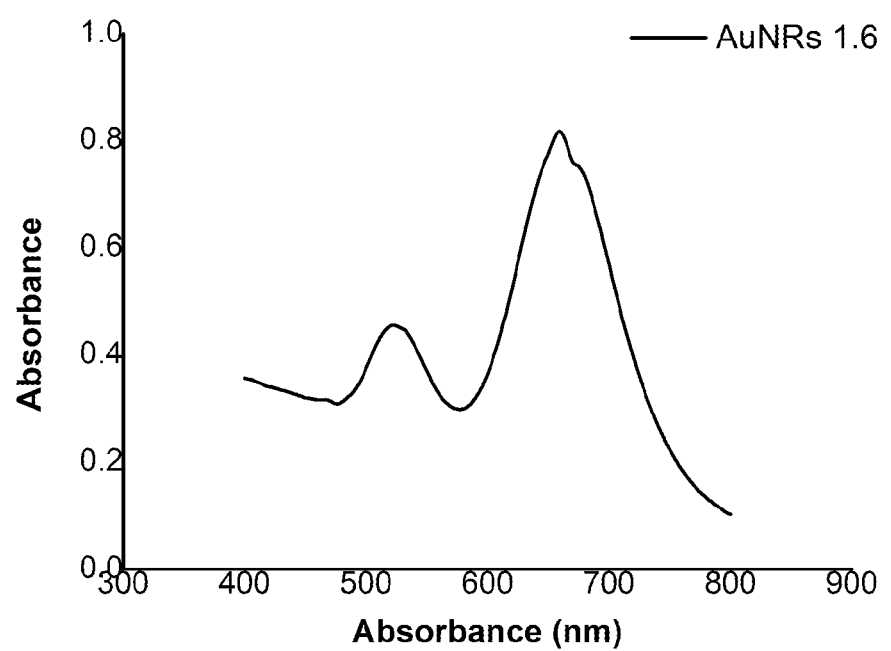
FIG. 5 shows UV-Vis spectrum of the rod-shaped gold nanoparticle having an aspect ratio of 1.73 and produced in Example 1-2.
Figure 6:
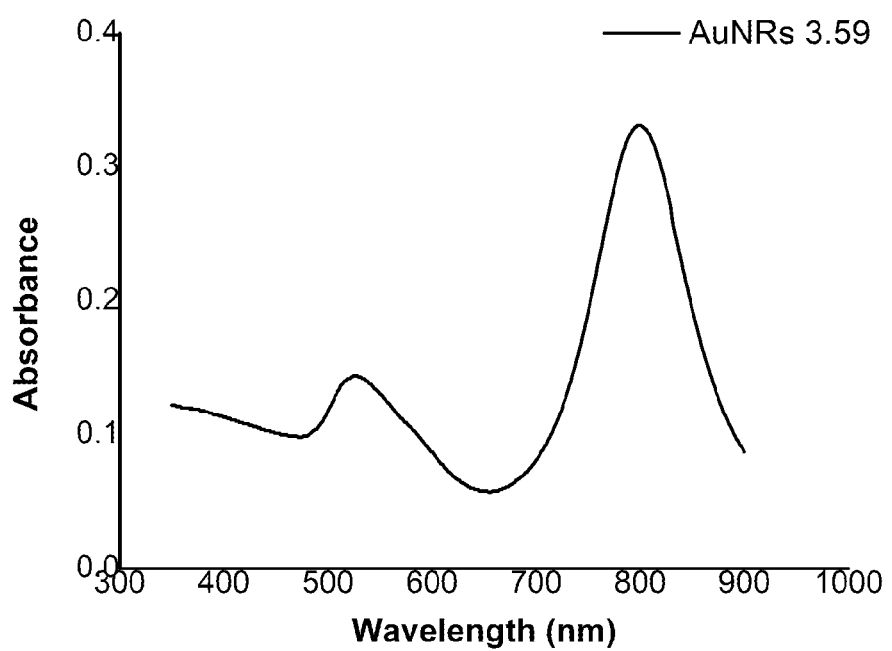
FIG. 6 shows UV-Vis spectrum of the rod-shaped gold nanoparticle having an aspect ratio of 3.59 and produced in Example 1-3.
Figure 7:
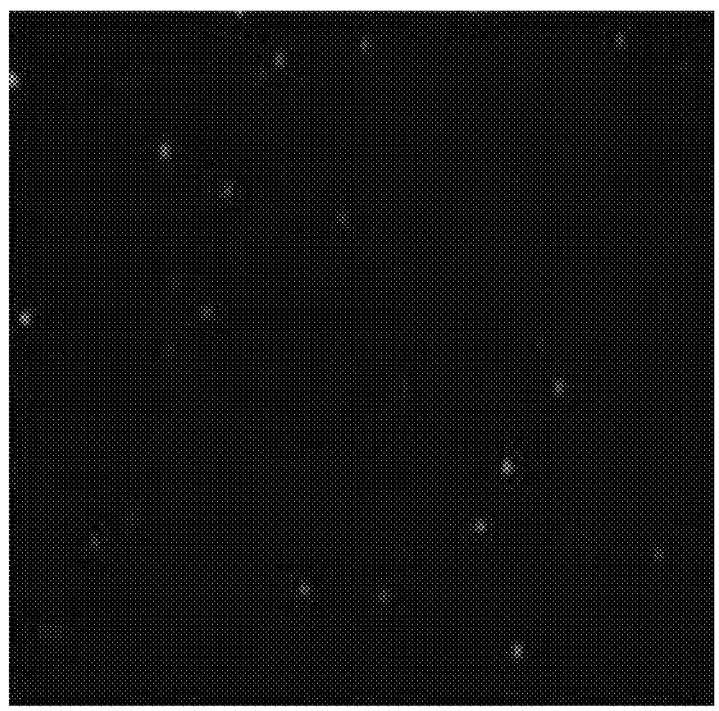
FIG. 7 shows a dark field image of the 50 nm-sized circular gold nanoparticle produced in Example 1-1 exposed at 1000 times magnification.
Figure 8:
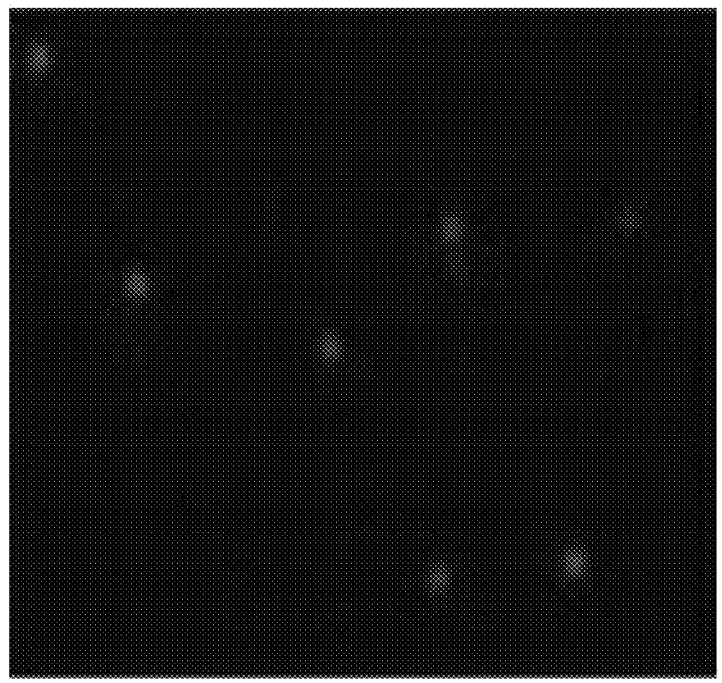
FIG. 8 shows a dark field image of the rod-shaped gold nanoparticle having an aspect ratio of 1.73 produced in Example 1-2 exposed at 1000 times magnification.

Unless defined otherwise, all the technical and scientific terms used herein have the same meanings as those generally understood by persons skilled in the art to which the present invention pertains. In general, nomenclature used in the present specification is well known and generally used in the present technical field.

The present invention relates to a nanoplasmonic biosensor for diagnosing Alzheimer's disease capable of simultaneously detecting Alzheimer's disease onset markers.

In the present invention, taking into account the fact that 500 ml of cerebrospinal fluid flows into blood every day, and an onset mechanism of Alzheimer's disease occurring in the brain is fully reflected in the blood, it has been attempted to develop a nanoplasmonic biosensor capable of simultaneously detecting the Alzheimer's disease onset markers in a blood sample.

In the present invention, each antibody or aptamer that binds to Alzheimer's disease onset marker, Aβ 1-40(beta-amyloid 40) peptide, Aβ 1-42(beta-amyloid 42) peptide, or τ(tau) protein was immobilized to a circular gold nanoparticle, or rod-shaped gold nanoparticles each having an aspect ratio of 1.73 and an aspect ratio of 3.59, and the distinguished optical and visual characteristics of the gold nanoparticles were used to confirm the Alzheimer's disease onset markers. The gold nanoparticles having different shapes and sizes are able to perform colorimetric analysis through surface resonance plasmonic spectrum showing different maximum wavelengths and dark field image. At this time, the antibody or the aptamer of the onset marker was connected by treating heterofunctional polyethylene glycol (SH-PEG-COOH) with the gold nanoparticles. By using the fact that resonance occurs in a larger wavelength region when the gold nanoparticles bind to the onset marker, whether the corresponding onset marker is present was confirmed through a change in spectrum of the nanoparticle that binds to the antibody or the aptamer of the specific onset marker. Meanwhile, it was confirmed that it was possible to quantify the onset marker by standardizing maximum wavelength mobility that occurred when an artificially synthesized marker was applied to a sensor, and thus it was found that the nanoplasmonic biosensor of the present invention was able to detect the Alzheimer's disease onset marker with very high sensitivity and accuracy.

Accordingly, in an aspect, the present invention provides a method for diagnosing Alzheimer's disease comprising (A) contacting a sample separated from a specimen with a plasmonic sensor based on a gold nanoparticle to which an antibody or an aptamer specific to a target protein of which expression is specifically increased or decreased in Alzheimer's patient is immobilized, thereby inducing a binding between the target protein and the antibody or the aptamer; (B) measuring light scattering spectrum according to the binding; and (C) determining whether or not Alzheimer's disease occurs through analysis of maximum wavelength mobility (Δλmax) obtained from the spectrum.

In the present invention, the sample may be utilized as long as it is a body fluid discharged from a human body, and it is particularly preferable that the sample is blood in view of the fact that the cerebrospinal fluid flows into the blood.

In the present invention, the target protein may be one or more selected from the group consisting of Aβ 1-40(beta-amyloid 40) peptide, Aβ 1-42(beta-amyloid 42) peptide, and τ(tau) protein, but is not limited thereto.

In the present invention, non-limiting examples of the antibody or the aptamer specific to Aβ 1-40(beta-amyloid 40) peptide include anti-beta amyloid 1-40 antibody (abcam, ab20068), anti-beta amyloid 1-40 antibody (abcam, ab12265), beta amyloid (1-40) polyclonal antibody (Invitrogen, 44-136), beta amyloid (1-40) polyclonal antibody (Invitrogen, 44-348A), A beta 40 antibody (Novus bio, NB30-225SS), anti-amyloid beta 1-40 antibody (QED Bioscience Inc., 57002), anti amyloid beta (1-40) (OriGene Technologies, DM410-05), amyloid beta peptide 1-40 (Ab1-40) antibody (Abbexa Ltd., abx132222), anti-amyloid beta peptide 1-40 antibody (MyBioSoirce.com, MBS2099585), and amyloid beta (1-40/42) antibody (Biorbyt, orb26764).

In the present invention, non-limiting examples of the antibody or the aptamer specific to τ(tau) protein include tau monoclonal antibody (HT7) (Invitrogen, MN1000), tau antibody (TAU-5) (santa cruz, sc-58860), tau, total (TAU-5) (alzforum, MAB361), tau antibody (TAU-5) (novus, nb200-514), and tau monoclonal antibody (TAU-5) (absolute antibody).

In the present invention, non-limiting examples of the antibody or the aptamer specific to Aβ 1-42(beta-amyloid 42) peptide include anti-beta amyloid 1-42 antibody (Sigma-Aldrich, AB5078P), anti-beta amyloid 1-42 antibody (Abcam, ab12267), anti-beta amyloid 1-42 antibody (Abcam, ab10148) anti-beta amyloid 1-42 antibody (BioLegend, Previously Covance catalog # SIG-39142), anti-beta amyloid 1-42 antibody (Merck (Millipore), AB5078P), and anti-beta amyloid 1-42 antibody (Arigo, ARG11044).

In the present invention, the gold nanoparticle may differ in shape and/or size depending on a type of antibody or aptamer that is immobilized. In other words, by producing and using gold nanoparticles having different shapes and/or sizes as the number of antibodies or aptamers that bind to each of a plurality of target proteins, various target proteins may be simultaneously detected and thus accuracy of diagnosis of Alzheimer's disease is improved.

In the present invention, the binding between the target protein and the antibody or the aptamer may be induced in a reaction sample containing a chaotropic solvent, thereby complementing a decrease in detection due to binding between an onset marker present in blood and other proteins. In this case, since the chaotropic solvent has a property of weakening a non-covalent bond between molecules by interfering with arrangement of water molecules present in a solvent, when added to blood, it serves to increase sensitivity of Alzheimer's disease onset marker.

In the present invention, the binding between the target protein and the antibody or the aptamer may be induced in a reaction sample containing a chaotropic solvent.

In addition, in the present invention, before inducing a binding between the target protein and the antibody or the aptamer, the blood may be pretreated with a solution containing a chaotropic solvent.

In the present invention, the chaotropic solvent may be any one selected from the group consisting of guanidine hydrochloride, guanidine thiocyanate, potassium thiocyanate, and sodium trichloroacetate, but is not limited thereto.

In the present invention, the chaotropic solvent for detection of Aβ 1-42 is preferably 5M to 7M guanidine hydrochloride or 2M to 5M guanidine thiocyanate, but is not limited thereto.

In the present invention, the chaotropic solvent for detection of τ protein is preferably 5M to 8M guanidine hydrochloride, more preferably about 6M, or 3.5M to 5.5M guanidine thiocyanate, but is not limited thereto.

In the present invention, the chaotropic solvent for detection of Aβ 1-40 is preferably 0.5-3M potassium thiocyanate, 0.5-3M guanidine thiocyanate or 2-8M guanidine hydrochloride, but is not limited thereto.

In the present invention, the chaotropic solvent for detection of τ protein and Aβ 1-40 is preferably 5M to 8M guanidine hydrochloride In the present invention, the maximum wavelength mobility (i.e. LSPR $\lambda_{max}$ shift) may be represented by a concentration of an onset factor that binds to a surface of the plasmonic sensor.

Meanwhile, the present invention also provides a biosensor for detecting Alzheimer's disease in which an antibody or an aptamer of at least any one target protein selected from the group consisting of Aβ 1-40 peptide, Aβ 1-42 peptide, and τ protein is immobilized to a gold nanoparticle.

In the present invention, the gold nanoparticle may differ in shape and/or size depending on a type of the antibody or the aptamer immobilized thereto.

In the present invention, an average particle size of the gold nanoparticle is preferably 10 to 150 nm, and more preferably 40 to 130 nm. Meanwhile, when the gold nanoparticle has a circular shape, a diameter is preferably 40 to 60 nm, and more preferably about 50 nm, and when the gold nanoparticle has a rod shape, an aspect ratio is preferably 1 to 5, and more preferably 1.6 to 3.7.

Hereinafter, the present invention will be described in detail with reference to the following Examples. However, the following examples are only for exemplifying the present invention, and it will be obvious to those skilled in the art that the scope of the present invention is not construed to be limited to these examples.

Example 1 Production of Gold Nanoparticle

In order to produce a nanoplasmonic biosensor based on the surface plasmon resonance phenomenon of the present invention, a 50 nm-sized circular gold nanoparticle, a rod-shaped gold nanoparticle having an aspect ratio of 1.73, and a rod-shaped gold nanoparticle having an aspect ratio of 3.59 were synthesized by a method known in the art (i.e. wet synthesis), and materials used in the synthesis were purchased from Sigma Aldrich (USA).

1-1. Production of 50 nm-Sized Circular Gold Nanoparticle 10 ml of 0.1M $HAuCl_4$ and 9.9 ml of sterilized water were mixed in a 20 ml vial and heated at 200° C. while stirring at 1000 to 1500 rpm until boiling. 1 ml of 0.04M sodium citrate was added to the boiled gold aqueous solution, and when the yellow aqueous solution was changed to wine color, the solution was maintained for 5 minutes and then stirred at 1150 rpm at room temperature. After the reaction was completed, the solution was filtered by a 0.2 µl filter to remove an aggregated product, and a size and a shape were measured by using a high resolution transmission electron microscopy (HR-TEM, jEOL JEM-3011) and a UV/VIS spectrophotometer (UV/VIS 3600, Shimadzu).

1-2. Production of Rod-Shaped Gold Nanoparticle Having Aspect Ratio of 1.73

For a gold nanoparticle seed solution, 5 ml of 0.5 mM $HAuCl_4$ and 5 ml of 0.2 M CTAB were mixed, and 1 ml of 0.006 M $NaBH_4$ was added. The Au(III)-CTAB aqueous solution was stirred at 1200 rpm. The seed solution was used after a color of the solution was changed from yellow to yellowish brown, and the seed solution was aged at room temperature for 30 minutes before use.

For a growth solution, 1.4 g of CTAB and 0.2468 g of NaOL were dissolved in sterilized water at 50° C., then a temperature of the solution was lowered to 30° C., and 2.4 ml of 4 mM $AgNO_3$ was added, and the solution was left for 15 minutes without stirring. Then, when 50 ml of 1 mM $HAuCl_4$ was added and the solution was stirred at 700 rpm for 90 minutes, the color of the aqueous solution disappeared (colorless). 0.3 ml of 37 wt. % (12.1 M) HCl was added and stirred at 400 rpm for 15 minutes to adjust pH. 0.25 ml of 0.064 M ascorbic acid was added and vigorously stirred for 30 seconds, and 0.04 ml of the seed solution was added and vigorously stirred for 30 seconds. Then, the mixture was allowed to grow at 30° C. for 12 hours without stirring. At this time, the color changed to purple. Then, the product was separated by centrifugation at 7000 rpm for 30 minutes, and the supernatant was removed. A size and a shape were measured by using a high resolution transmission electron microscopy (HR-TEM, jEOL JEM-3011) and a UV/VIS spectrophotometer (UV/VIS 3600, Shimadzu).

1-3. Production of Rod-Shaped Gold Nanoparticle Having Aspect Ratio of 3.59

For a gold nanoparticle seed solution, 5 ml of 0.5 mM $HAuCl_4$ and 5 ml of 0.2 M CTAB were mixed, and 1 ml of 0.006 M $NaBH_4$ was added. The Au(III)-CTAB aqueous solution was stirred at 1200 rpm. The seed solution was used after a color of the solution was changed from yellow to yellowish brown, and the seed solution was aged at room temperature for 30 minutes before use.

For a growth solution, 1.8 g of CTAB and 0.2468 g of NaOL were dissolved in sterilized water at 50° C., then a temperature of the solution was lowered to 30° C., and 4.8 ml of 4 mM $AgNO_3$ was added, and the solution was left for 15 minutes without stirring. Then, when 50 ml of 1 mM $HAuCl_4$ was added and the solution was stirred at 700 rpm for 90 minutes, the color of the aqueous solution disappeared (colorless). 0.42 ml of 37 wt. % (12.1 M) HCl was added and stirred at 400 rpm for 15 minutes to adjust pH. 0.25 ml of 0.064 M ascorbic acid was added and vigorously stirred for 30 seconds, and 0.04 ml of the seed solution was added and vigorously stirred for 30 seconds. Then, the mixture was allowed to grow at 30° C. for 12 hours without stirring. At this time, the color changed to purple. Then, the product was separated by centrifugation at 7000 rpm for 30 minutes, and the supernatant was removed. A size and a shape were measured by using a high resolution transmission electron microscopy (HR-TEM, jEOL JEM-3011) and a UV/VIS spectrophotometer (UV/VIS 3600, Shimadzu).

As a result, it was confirmed that the about 50 nm-sized circular gold nanoparticle (FIG. 1), the rod-shaped gold nanoparticle having an aspect ratio of 1.73 (FIG. 2), and the rod-shaped gold nanoparticle having an aspect ratio of 3.59 (FIG. 3) were produced, respectively, and it could be confirmed that different optical and visual characteristics were induced in the circular gold nanoparticle and the rod-shaped gold nanoparticles (FIGS. 4 to 9). Meanwhile, by mixing and observing the circular and rod-shaped gold nanoparticles (FIG. 10), it could be confirmed that surface resonance plasmonic spectrum showing different maximum wavelengths (FIG. 11) and colorimetry through a dark field image (FIG. 12) were observed even in a state in which each of these gold nanoparticles were mixed.

Example 2: Manufacture of Substrate

A glass substrate which is a support of a nanoplasmonic sensor was surface treated with a silane compound including an amine or alkyl end group. The silane compound was (3-aminopropyl)triethoxysilane, and an amine group was attached to the substrate by immersing the glass substrate in 5% (3-aminopropyl)triethoxysilane solution for 15 minutes.

Example 3: Manufacture of Nanoplasmonic Biosensor Substrate in which Antibody Binds to Circular Gold Nanoparticle A circular gold nanoparticle was treated with heterofunctional polyethylene glycol (SH-PEG-COOH), and an antibody with respect to Alzheimer's disease onset marker of Aβ 1-40 was bound thereto. Here, the used heterofunctional polyethylene glycol (SH-PEG-COOH) had a molecular weight of 2000 and was purchased from Laysan Bio. Ltd. The heterofunctional polyethylene glycol (SH-PEG-COOH) acted as a stabilizer, and provided a functional group that allowed the gold nanoparticle to adhere well to a glass substrate, and further, that was bindable to the antibody. 2 mg of SH-PEG-COOH having a molecular weight of 2000 was dissolved in 1 ml of sterilized water to prepare a solution of 1 mM. Thereafter, 20 µl of the above prepared solution was added to 1 ml of the 50 nm-sized circular gold nanoparticle aqueous solution synthesized in Example 1-1, stirred for 24 hours, and centrifuged at 7000 rpm for 15 minutes to separate the surface-treated gold nanoparticle. The separated pellet was resuspended in sterilized water to an optical density of 2, and 1 µl of 0.7 M 1-ethyl-3-(3-dimethylaminopropyl)carbodiimide/N-hydrosuccimide (EDC/NHS) was added based on 100 µl of the gold aqueous solution and mixed well, followed by incubation for 15 minutes. In the meantime, 50 µl of Aβ 1-40 antibody (anti-beta amyloid 1-40 antibody (abcam, ab20068); or beta amyloid (1-40) polyclonal antibody (Invitrogen, 44-136)) to be attached to a surface of the gold nanoparticle was diluted with PBS to a concentration of 50 µg/ml. After 15 minutes, the antibody diluent was added to the PEG-treated gold aqueous solution, and pippeted, and reacted without stirring for 4 hours. After 4 hours, the reaction mixture was centrifuged at 5000 rpm for 10 minutes and redispersed in 100 µl of sterilized water.

The antibody-bound circular gold nanoparticle aqueous solution was diluted to an optical density of 0.05, and then 10 µl of the gold nanoparticle aqueous solution was dropped on the glass substrate. Thereafter, the gold nanoparticle aqueous solution was removed again after about 50 seconds.

Upon reviewing a change in UV-Vis spectrum wavelength shown for each step in binding the antibody to the circular gold nanoparticle, plasmonic spectrum of the 50 nm-sized circular gold nanoparticle produced in Example 1-1 had a peak at 530.5 nm (FIG. 14, 50 nm bare AuNPs). However, Rayleigh light scattering spectrum of the same single nanoparticle after surface treatment with 1 mM of heterofunctional PEG having a molecular weight of 2000 had a peak at 533 nm (FIG. 14, PEGylated 50 nm AuNPs), and when 50 µl of antibody at a concentration of 50 µg/ml was attached to the surface of the gold nanoparticle, and reacted for 4 hours, a peak appeared at 537.2 nm (FIG. 14, 50 µg/ml antibody binding). In other words, it could be confirmed that as compared to the circular gold nanoparticle, the UV-Vis maximum wavelength shift of 2.5 nm after the PEG was attached, and the UV-Vis maximum wavelength shift of 4.2 nm after the antibody was attached were observed.

Figure 15:
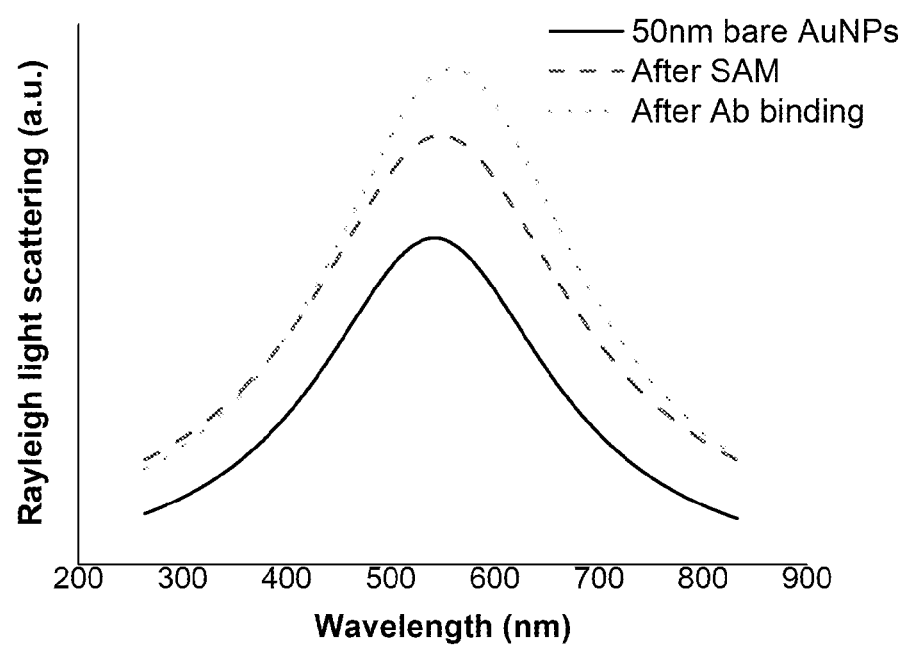
FIG. 15 shows LSPR light scattering shift spectrum shown for each step in binding PEG and an antibody to the circular gold nanoparticle.

Meanwhile, in the case of the LSPR light scattering shift spectrum shown for each step in binding the antibody to the circular gold nanoparticle, it could be confirmed that as compared to the plasmonic spectrum of the 50 nm-sized circular gold nanoparticles prepared in Example 1-1 (FIG. 15, 50 nm bare AuNPs), the Rayleigh light scattering spectrum of the same single nanoparticle after surface treatment with 1 mM of heterofunctional PEG having a molecular weight of 2000 (FIG. 15, after SAM) showed the LSPR maximum wavelength shift of 17.3 nm, and the spectrum after 50 µl of antibody at a concentration of 50 µg/ml was attached to the surface of the gold nanoparticle (FIG. 15, after ab binding) showed the LSPR $\lambda_{max}$ shift of 31 nm, respectively.

Example 4: Manufacture of Nanoplasmonic Biosensor in which Antibody Binds to Rod-Shaped Gold Nanoparticle A rod-shaped gold nanoparticle was treated with heterofunctional polyethylene glycol (SH-PEG-COOH), and antibodies with respect to two Alzheimer's disease onset markers of Aβ 1-42 (anti-beta amyloid 1-42 antibody (Abcam, ab10148); or anti-beta amyloid 1-42 antibody (Merck (Millipore), AB5078P)) and τ protein (tau monoclonal antibody (HT7) (Invitrogen, MN1000) were bound thereto. Here, the used heterofunctional polyethylene glycol (SH-PEG-COOH) had molecular weight of 2000 and 3400, respectively, and purchased from Laysan Bio. Ltd. The heterofunctional polyethylene glycol (SH-PEG-COOH) acted as a stabilizer, and provided a functional group that allowed the gold nanoparticle instead of the CTAB of the surface of the rod-shaped gold nanoparticles having the aspect ratio of 1.73 and 3.59 to adhere well to the glass substrate, and further, that was bindable to the antibody. 53.5 µl of 300 µg Au/ml of the rod-shaped gold nanoparticle having the aspect ratio of 3.59 and 50 mg of SH-PEG-COOH having a molecular weight of 3400 were added to 1946.5 µl of sterilized water. In the case of the rod-shaped gold nanoparticle having the aspect ratio of 1.73, 37.05 µl of 300 µg Au/ml of the rod-shaped gold nanoparticle having the aspect ratio of 1.73 and 40 mg of SH-PEG-COOH having a molecular weight of 3400 were added to 1962.95 µl of sterilized water. The solution was rotation-stirred for 4 days at room temperature to 200 rpm and then centrifuged at 5000 rpm for 4 minutes. The SH-PEG-COOH that did not bind to the gold was removed by the centrifugation, and the solution was resuspended in 1 mL of sterilized water. Then, EDC and NHS were used to connect the gold nanoparticle and the antibody. The rod-shaped gold nanoparticle aqueous solution was diluted to an optical density of 0.1, and then 10 µl of the gold nanoparticle aqueous solution was dropped on the glass substrate. Thereafter, the gold nanoparticle aqueous solution was removed again after about 5 minutes.

Example 5: Verification of Nanoplasmonic Biosensor Effect

By using phenomenon that when the gold nanoparticle binds to a biomolecule, resonance occurs in a larger wavelength region, spectrum changes of the nanoparticle in which the Aβ 1-40, Aβ 1-42, and τ protein were bound to the antibody were observed, and whether or not the corresponding Alzheimer's disease onset factor was present was confirmed.

That is, it was confirmed that the antigen-specific binding was surely generated without cross-talk in the biosensors manufactured in Examples 3 and 4, wherein all the antigens were added at 100 nM, and the PBS was used as a diluting solution.

Figure 16:
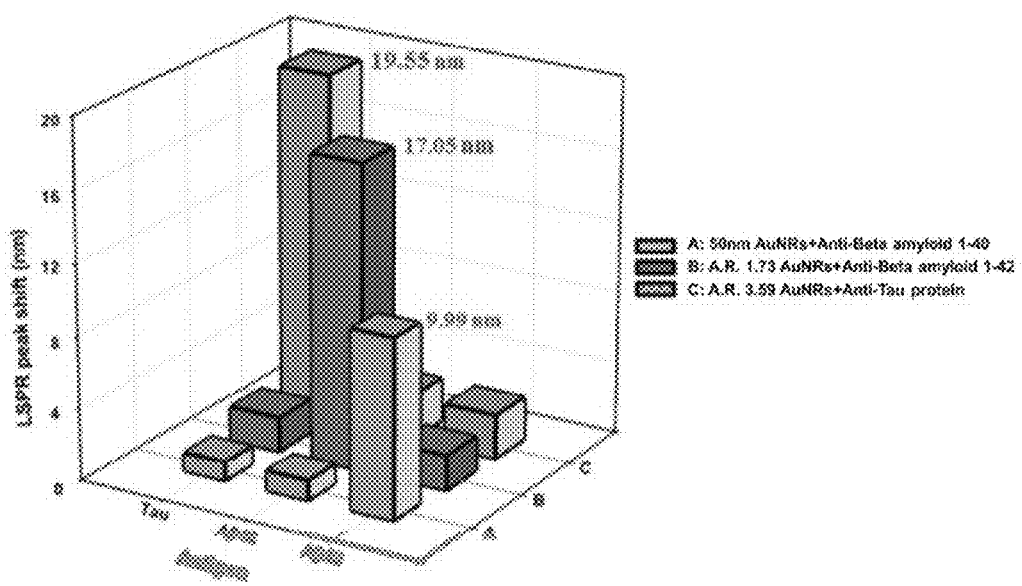
FIG. 16 shows the LSPR $\lambda_{max}$ shift of shape-code plasmon biosensors for the independent detection of Aβ 1-40, Aβ 1-42 and τ protein.

In a 50 nm-sized circular gold nanoparticle biosensor manufactured by Example 3, the maximum Rayleigh light scattering wavelength shift of about 10 nm was shown for Aβ 1-40 antibody since it reacted only with 100 nM of Aβ 1-40 due to the Aβ 1-40 antibody immobilized to the surface, and the shifts of just 1.4 nm and 1.1 nm were shown for 100 nM of Aβ 1-42 and τ protein, respectively. Meanwhile, in a rod-shaped gold nanoparticle biosensor having the aspect ratio of 1.73 manufactured by Example 4, since the Aβ 1-42 was immobilized to the surface of the particle, the maximum scattering wavelength shift of 17 nm was shown for 100 nM Aβ 1-42, but the maximum scattering wavelength shifts of just about 1.95 nm and 1.93 nm were shown for the Aβ 1-40 and τ protein at the same concentration, respectively. In addition, in a rod-shaped gold nanoparticle biosensor having the aspect ratio of 3.59 manufactured by Example 4, since the τ protein antibody was immobilized, the maximum scattering wavelength shift of 19 nm was shown for 100 nM T protein, but the maximum scattering wavelength shifts of just about 2.45 nm and 2.5 nm were shown for the two kinds of beta-amyloid and τ protein at the same concentration, respectively (FIG. 16).

Figure 17A:
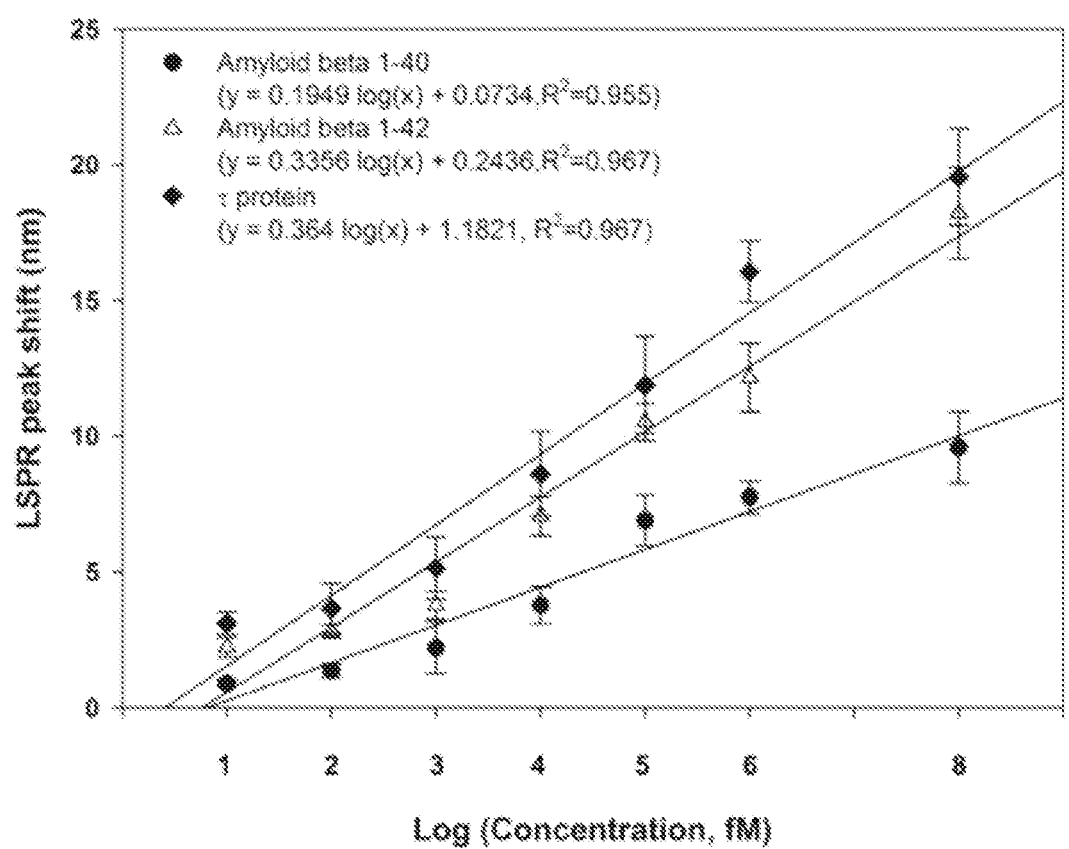
FIG. 17A shows linear regression of the calibration curve describing the relationship between the LSPR $\lambda_{max}$ shifts and Aβ 1-40, Aβ 1-42 and τ protein concentrations.
Figure 17B:
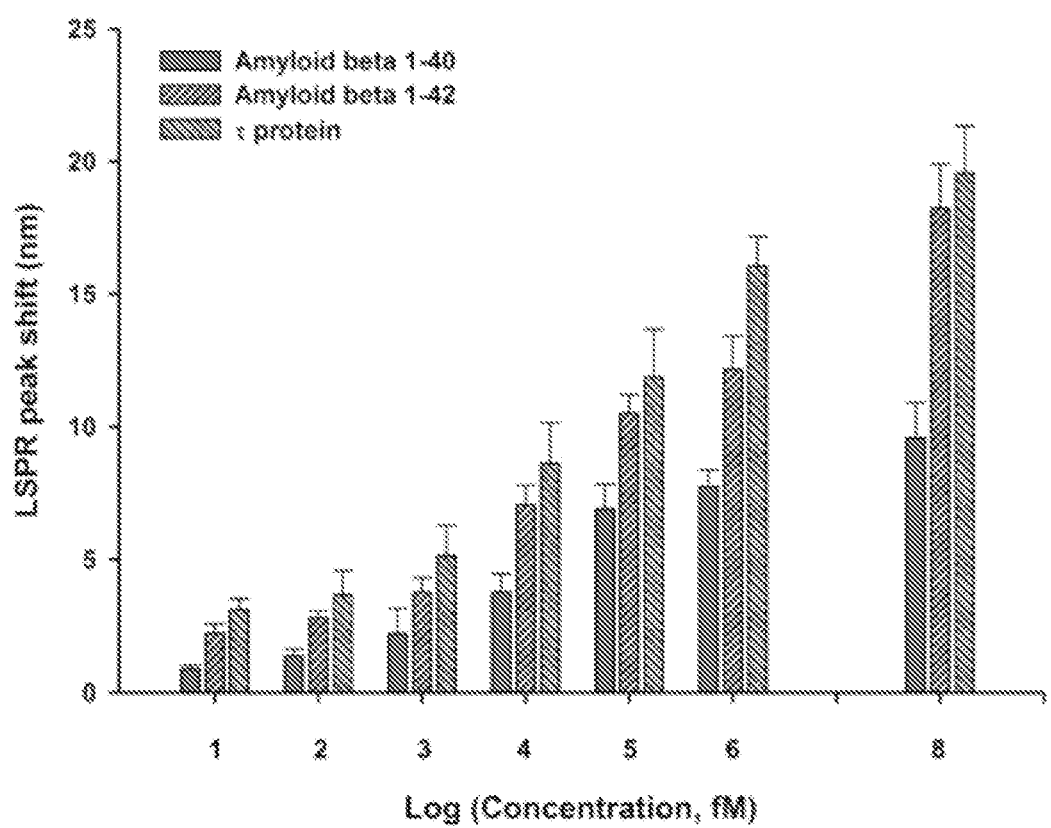
FIG. 17B shows detection of Aβ 1-40, Aβ 1-42 and τ protein at concentrations ranging from 10 fM to $10^8$ fM using mimic plasma.

Under biological conditions of patient-mimicked plasma, multiple biomarkers detection was conducted on a platform consisting of three types immunogold with three Alzheimer's disease biomarkers, Aβ 1-40, Aβ 1-42 and τ protein. LSPR Δλmax shifts indicated a strong linearity with the concentration logarithm in the range from $1*10^1$ fM to $1*10^8$ fM that concentrations are optimized between least twenty times lower and quite higher than levels of biomarkers in AD patient plasma (FIG. 17A). Many coefficients of determination ($R^2$) were over 0.95 meaning the values of LSPR $\lambda_{max}$ shift are significantly depended on concentrations of samples in mimicked blood. The limit of detection (LOD) values of the biosensor were calculated by this formula: LOD=3*δ/slope, where δ is the standard deviation of blank and slope is the slope of calibration curve. Calculated values were 34.9 fM for Aβ 1-40 with immune 50 nm gold nanosphere, 26 fM for Aβ 1-42 with immune-aspect ratio 1.73 of gold nanorod and 23.6 fM for τ protein with immune-aspect ratio 3.59 of gold nanorod (FIG. 17B).

Example 6: Enzyme Immunoassay of Aβ 1-42 According to Chaotropic Solvent

Ammonium bicarbonate (ABC) was dissolved in water to prepare a 25 mM aqueous solution. Then, guanidine hydrochloride, guanidine thiocyanate, or potassium thiocyanate was dissolved in the 25 mM ammonium bicarbonate (ABC) aqueous solution prepared above to prepare a 20 M stock solution.

TABLE 1

Concentration of a chaotropic solvent for enzyme immunoassay of Aβ 1-42

| Blood | 50 μl | 50 μl | 50 μl | 50 μl | 50 μl | 50 μl | 50 μl | 50 μl | 50 μl |
|---|---|---|---|---|---|---|---|---|---|
| Diluting Solution | 50 μl | 47.5 μl | 45 μl | 40 μl | 35 μl | 30 μl | 25 μl | 20 μl | 10 μl |
| guanidine hydrochloride (20M), guanidine thiocyanate (20M) or potassium thiocyanate (20M) | — | 2.5 μl | 5 μl | 10 μl | 15 μl | 20 μl | 25 μl | 30 μl | 40 μl |
| Final concentration (M) | 0 | 0.5 | 1 | 2 | 3 | 4 | 5 | 6 | 8 |

A concentration of the chaotropic solvent was shown above, and analysis was performed according to the instruction of enzyme immunoassay kit (SensoLyte™, Catalog # AS-55552) of Aβ 1-42. Human blood was used as a sample, and plasma in which an aggregate was removed from the blood was used to perform the experiments.

To briefly describe the experimental method, a human Aβ 1-42 standard (Component B) was reconstituted to be 1 ml of peptide standard reconstitution buffer (Component G). In other words, the peptide was hydrated for 10 minutes, reversed upside down and mixed gently. 100 μl of the reconstituted standard per vial was dispensed and stored at −80° C. before use.

The strips (Component A) were aligned and labeled according to the number of wells used in the standard and the sample, and then the dilution standard and the sample were each subjected to duplicate dispensing. Sequential dilution of the human Aβ 1-42 standard was prepared immediately before the experiment, and proceeded as described in Table 2 below.

TABLE 2

| Step | Concentration, pg/mL | Aβ42 Standard (Component B) | Sample Dilution Buffer (Component C) |
|---|---|---|---|
| 1 | 1,000,000 | Prepare as described in 1.1 | |
| 2 | 10,000 | 10 μL from step 1 | 990 μL |
| 3 | 250 | 25 μL from step 2 | 975 μL |
| 4 | 125 | 500 μL from step 3 | 500 μL |
| 5 | 62.5 | 500 μL from step 4 | 500 μL |
| 6 | 31.25 | 500 μL from step 5 | 500 μL |
| 7 | 15.625 | 500 μL from step 6 | 500 μL |
| 8 | 7.8125 | 500 μL from step 7 | 500 μL |
| 9 | 3.91 | 500 μL from step 8 | 500 μL |

A detection antibody (Component H) was diluted 200-fold with a detection antibody dilution buffer (Component I). 50 μl of the antibody solution was dispensed into each well, and 100 μl of the diluted Aβ 1-42 standard including the blank was subjected to duplicate dispensing into each well. Meanwhile, 100 μl of the diluted sample as shown in Table 1 above was added to each well, and 50 μl of the antibody solution was added to each well. The plate was covered with an adhesive plate cover (Component J) and allowed to react by blocking light at 4° C. overnight. A 10× wash buffer (Component D) was diluted with distilled water to prepare a 1× wash buffer, the solution of the plate reacted overnight was removed, and the plate was washed 6 to 7 times in each well using 350 μl of 1× wash buffer. Between each wash process before the wash solution was removed, time was taken to allow the wash buffer to fully act for 20 seconds. The plate was cleaned using a paper towel for accurate optical reading. 100 μl of TMB color substrate solution (Component E) was added to each well, and the plate was lightly tapped and reacted at room temperature for about 5 to 15 minutes until a blue color gradient appeared along the well. 50 μl of termination solution (Component F) was added to each well and the plate was tapped lightly to turn blue color to yellow. Absorbance (OD) was measured at 450 nm using a microplate absorbance reader within 20 minutes after the termination solution was added.

Figure 18:
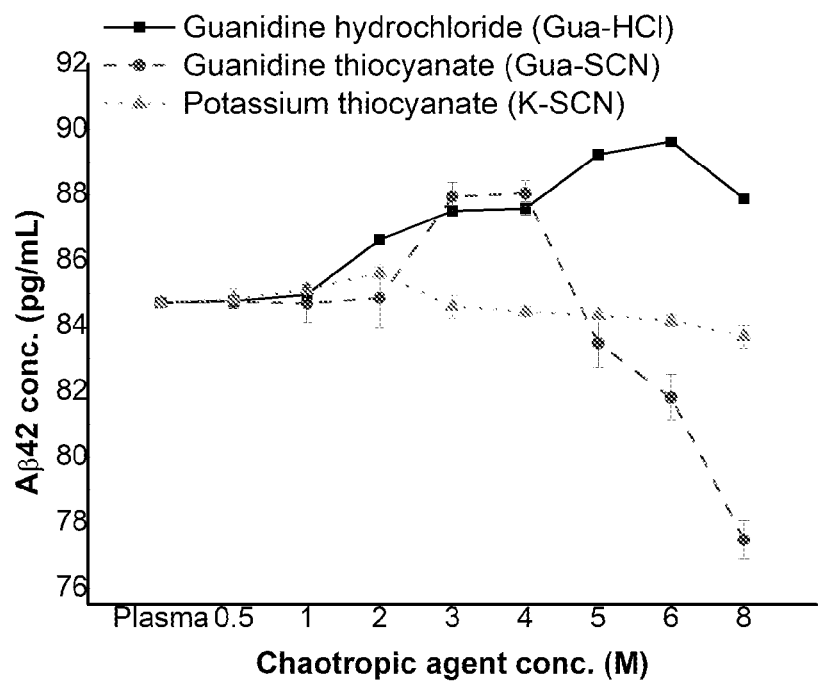
FIG. 18 shows a detection amount of Aβ 1-42 according to a concentration of a chaotropic solvent.

As a result, it could be confirmed that a detection amount of Aβ 1-42 was higher in 6M guanidine hydrochloride or 3M to 4M guanidine thiocyanate (FIG. 18).

Example 7: Enzyme Immunoassay of τ Protein According to Chaotropic Solvent

Ammonium bicarbonate (ABC) was dissolved in water to prepare a 25 mM aqueous solution. Then, guanidine hydrochloride, guanidine thiocyanate, and potassium thiocyanate were dissolved in the 25 mM ammonium bicarbonate (ABC) aqueous solution prepared above to prepare a 20 M stock solution.

TABLE 3

Concentration of a chaotropic solvent(guanidine hydrochloride) for enzyme immunoassay of τ protein

| Blood | 50 μl | 50 μl | 50 μl | 50 μl | 50 μl | 50 μl | 50 μl | 50 μl | 50 μl |
|---|---|---|---|---|---|---|---|---|---|
| Diluting Solution | 50 μl | 47.5 μl | 45 μl | 40 μl | 35 μl | 30 μl | 25 μl | 20 μl | 10 μl |
| Guanidine hydrochloride (20M) | — | 2.5 μl | 5 μl | 10 μl | 15 μl | 20 μl | 25 μl | 30 μl | 40 μl |
| Final concentration (M) | 0 | 0.5 | 1 | 2 | 3 | 4 | 5 | 6 | 8 |

TABLE 4

Concentration of a chaotropic solvent(guanidine thiocyanate) for enzyme immunoassay of τ protein

| Blood | 50 μl | 50 μl | 50 μl | 50 μl | 50 μl | 50 μl | 50 μl | 50 μl | 50 μl |
|---|---|---|---|---|---|---|---|---|---|
| Diluting Solution | 50 μl | 47.5 μl | 45 μl | 40 μl | 35 μl | 30 μl | 25 μl | 20 μl | 10 μl |
| guanidine thiocyanate (20M) | — | 2.5 μl | 5 μl | 10 μl | 15 μl | 20 μl | 25 μl | 30 μl | 40 μl |
| Final concentration (M) | 0 | 0.5 | 1 | 2 | 3 | 4 | 5 | 6 | 8 |

TABLE 5

Concentration of a chaotropic solvent(potassium thiocyanate) for enzyme immunoassay of τ protein

| Blood | 50 μl | 50 μl | 50 μl | 50 μl | 50 μl | 50 μl | 50 μl | 50 μl | 50 μl |
|---|---|---|---|---|---|---|---|---|---|
| Diluting Solution | 50 μl | 47.5 μl | 45 μl | 40 μl | 35 μl | 30 μl | 25 μl | 20 μl | 10 μl |
| potassium thiocyanate (20M) | — | 2.5 μl | 5 μl | 10 μl | 15 μl | 20 μl | 25 μl | 30 μl | 40 μl |
| Final concentration (M) | 0 | 0.5 | 1 | 2 | 3 | 4 | 5 | 6 | 8 |

A concentration of the chaotropic solvent was shown above, and analysis was performed according to the instruction of enzyme immunoassay kit (Invitrogen, Catalog nos. KHB0041, KHB0042) of τ protein. Human blood was used as a sample, and plasma in which the aggregate was removed from the blood was used to perform the experiments.

To briefly describe the experimental method, except for a chromogenic blank, 100 μl of a standard dilution buffer was added to a zero well. 100 μl of standard was added to an appropriate well for a standard curve, and 50 μl of sample and 50 μl of standard dilution buffer were added to a well for sample analysis. The plate was covered with a cover and allowed to react at room temperature for 2 hours, the solution was thoroughly removed by aspiration, and the plate was washed 4 times with 1× wash buffer. Then, 100 μl of human FGF-b Biotin conjugate solution was added to each well except the chromogenic blank, and mixed by tapping the side of the plate lightly. The plate was covered with a cover and allowed to react at room temperature for 1 hour, the solution was thoroughly removed by aspiration, and the plate was washed 4 times with 1× wash buffer. 100 μl of streptavidin-HRP was added to each well except for the chromogenic blank, and the plate was covered with a cover and allowed to react at room temperature for 30 minutes. The solution in each well was thoroughly removed by aspiration, and the plate was washed times with 1× wash buffer. 100 μl of stabilized chromogen was added to each well to allow each substrate solution to turn blue. The reaction was performed at room temperature under a dark condition for 30 minutes. 100 μl of the termination solution was added to each well, and for mixing, the side of the plate was tapped lightly to allow the solution in each well to be changed from blue to yellow.

Figure 19:
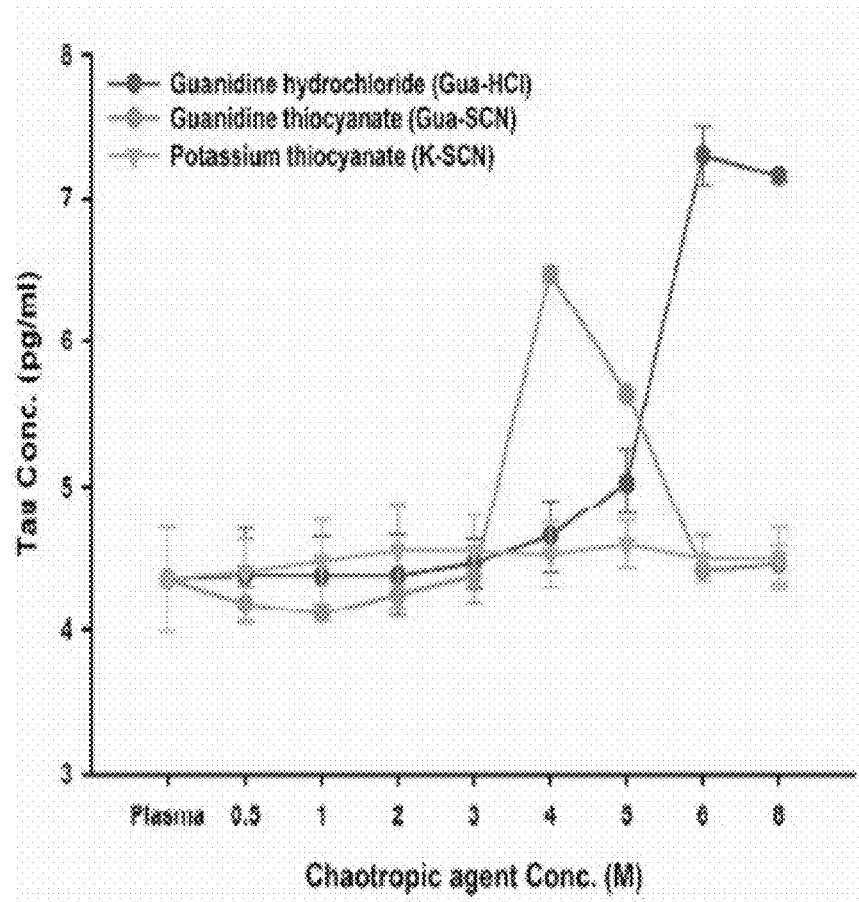
FIG. 19 shows a detection amount of τ protein according to the concentration of the chaotropic solvent.

As a result, it was confirmed that when the 6M guanidine hydrochloride or 4M guanidine thiocyanate was used, the τ protein was highly detected (FIG. 19).

Figure 21A:
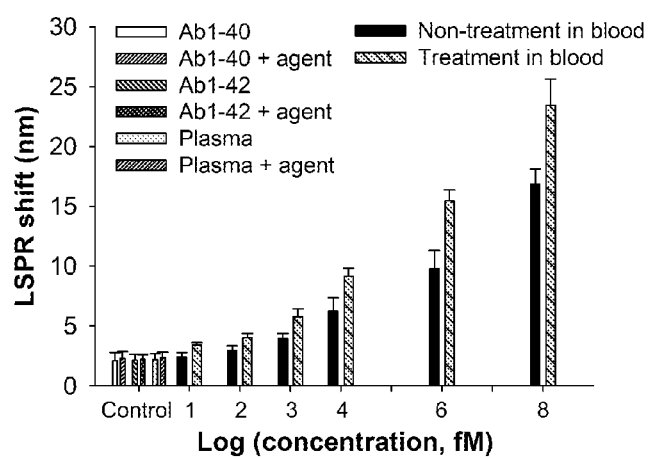
FIG. 21A shows detection of control (Aβ 1-40, Aβ 1-42 and pure plasma) and τ protein at concentrations ranging from 101 fM to 108 fM in plasma.
Figure 21B:
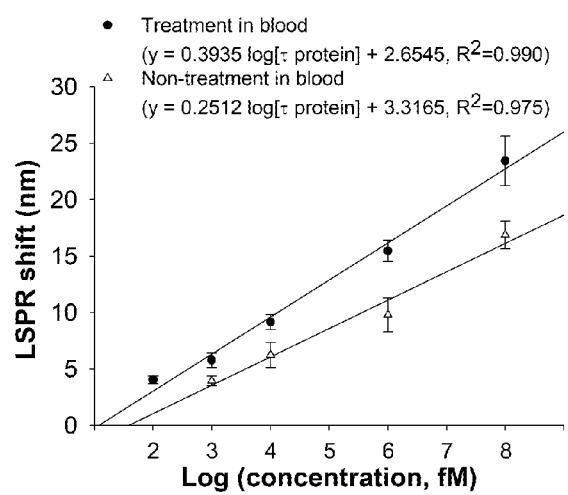
FIG. 21B shows linear regression of the calibration curve describing the relationship between the LSPR $\lambda_{max}$ shifts and τ protein concentrations.

We confirmed that the nanoplasmonic biosensor detected femtomolar amounts of τ protein from a fluid resembling blood and determined the detection limit of this sensor with/without chaotropic agent (FIGS. 21A and 21B). The T protein is present in minute amounts in peripheral blood, accompanied by large amounts of other proteins and biomolecules. To verify our platform, we monitored the LSPR $\lambda_{max}$ shift for τ protein concentrations from $1*10^1$ to $1*10^8$ fM in plasma both with and without 6 M Gua-HCl. The values increased when reactions occurred with τ protein in non-treated blood at concentrations from $10^4$ to $10^8$ fM (Black bars in FIG. 21A). However, no change was detected in a signal for concentrations below $10^3$ fM, indicating that the strong linearity of the signal response to the logarithm of the concentration only occurred within the range from $10^4$ to $10^8$ fM (White triangles in FIG. 18B). In addition, the limit of detection (LOD, 3*5/slope, where 5 is the standard deviation of 1, the blank and slope is the slope of calibration curve 46) was 1.56~1.66 pM, or approximately 1 pM τ protein in the absence of treatment. The known levels of τ protein in the blood of a patient with AD were approximately 239.13 fM~1.49 pM, and the minimal detectable values were 815.2 fM~2.72 pM based on existing blood-based practical and clinical assays such as double-sandwich ELISAs and IMR assays. In accordance with above-mentioned results and studies, this LSPR plasmonic biosensor without chaotropes was lacking in its detection of τ protein for the diagnosis of AD and lagged behind existing methods. Chaotropes hinder τ proteins from forming aggregates with themselves or plasma proteins. A greater amount of τ protein is consequently present and can bind immunogold, leading to larger changes in the refractive index around the gold nanoparticles. To enhance the sensitivity of these assays, we combined the LSPR plasmonic biosensor with the use of 6 M Gua-HCl as a chaotrope. This combination extended the linear dynamic range to reach from $10^2$ to $10^8$ fM with determination coefficients ($R^2$) of approximately 0.984 (Grey bars with hashes in FIG. 21A, black circles in FIG. 21B), and its minimum detectable concentration was 153.17-179.85 fM or approximately 100 fM τ protein (Black circles in FIG. 21B). These results therefore indicate that Gua-HCl enhanced the sensitivity of the τ protein specific plasmonic biosensor from the picomolar to the femtomolar scale, a ten-fold improvement; in addition, the assay's medical utility is improved using the chaotrope. Our proposed assay using the assistance of a chaotrope enables AD core protein levels to be used as clinical evidence, detecting the proteins with high sensitivity and quantifying them in a dynamic range from complex human biological fluids.

Example 8: Enzyme Immunoassay of Aβ 1-40 According to Chaotropic Solvent

Ammonium bicarbonate (ABC) was dissolved in water to prepare a 25 mM aqueous solution. Then, guanidine hydrochloride, guanidine thiocyanate, and potassium thiocyanate were dissolved in the 25 mM ammonium bicarbonate (ABC) aqueous solution prepared above to prepare a 20 M stock solution.

TABLE 6

Concentration of a chaotropic solvent (guanidine hydrochloride) for enzyme immunoassay of Aβ 1-40

| Blood | 50 μl | 50 μl | 50 μl | 50 μl | 50 μl | 50 μl | 50 μl | 50 μl | 50 μl |
|---|---|---|---|---|---|---|---|---|---|
| Diluting Solution | 50 μl | 47.5 μl | 45 μl | 40 μl | 35 μl | 30 μl | 25 μl | 20 μl | 10 μl |
| guanidine hydrochloride (20M) | — | 2.5 μl | 5 μl | 10 μl | 15 μl | 20 μl | 25 μl | 30 μl | 40 μl |
| Final Concentration (M) | 0 | 0.5 | 1 | 2 | 3 | 4 | 5 | 6 | 8 |

TABLE 7

Concentration of a chaotropic solvent (guanidine thiocyanate) for enzyme immunoassay of Aβ 1-40

| Blood | 50 μl | 50 μl | 50 μl | 50 μl | 50 μl | 50 μl | 50 μl | 50 μl | 50 μl |
|---|---|---|---|---|---|---|---|---|---|
| Diluting Solution | 50 μl | 47.5 μl | 45 μl | 40 μl | 35 μl | 30 μl | 25 μl | 20 μl | 10 μl |
| guanidine thiocyanate (20M) | — | 2.5 μl | 5 μl | 10 μl | 15 μl | 20 μl | 25 μl | 30 μl | 40 μl |
| Final concentration (M) | 0 | 0.5 | 1 | 2 | 3 | 4 | 5 | 6 | 8 |

TABLE 8

Concentration of a chaotropic solvent (potassium thiocyanate) for enzyme immunoassay of Aβ 1-40

| Blood | 50 μl | 50 μl | 50 μl | 50 μl | 50 μl | 50 μl | 50 μl | 50 μl | 50 μl |
|---|---|---|---|---|---|---|---|---|---|
| Diluting Solution | 50 μl | 47.5 μl | 45 μl | 40 μl | 35 μl | 30 μl | 25 μl | 20 μl | 10 μl |
| potassium thiocyanate (20M) | — | 2.5 μl | 5 μl | 10 μl | 15 μl | 20 μl | 25 μl | 30 μl | 40 μl |
| Final concentration (M) | 0 | 0.5 | 1 | 2 | 3 | 4 | 5 | 6 | 8 |

A concentration of the chaotropic solvent was shown above, and analysis was performed according to the instruction of enzyme immunoassay kit (Cusabio, Catalog no. CSB-E08299h) of Aβ 1-40. Human blood was used as a sample, and plasma in which the aggregate was removed from the blood was used to perform the experiments.

Figure 20:
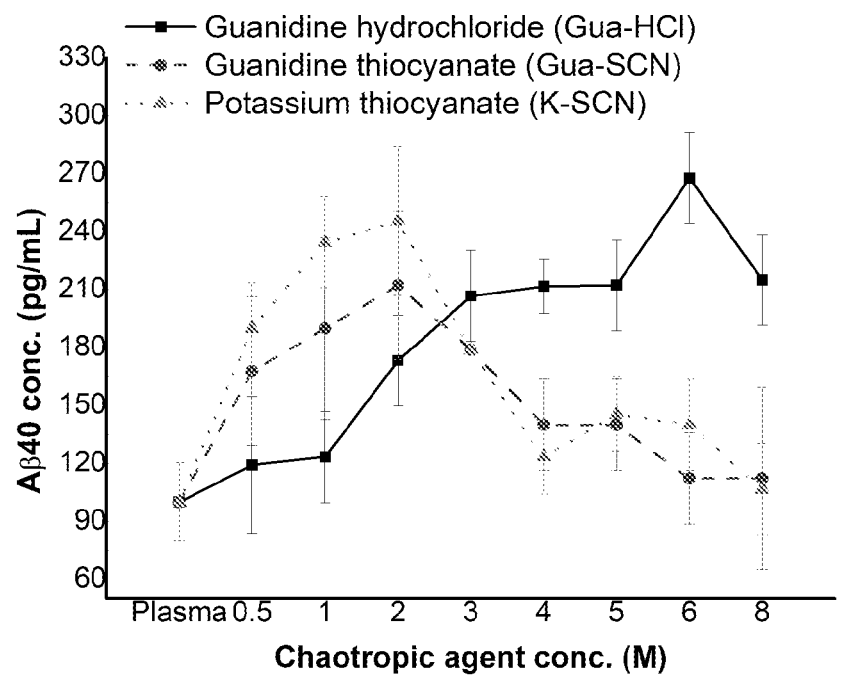
FIG. 20 shows a detection amount of Aβ 1-40 according to the concentration of the chaotropic solvent.

A detection amount of Aβ 1-40 according to the concentration of chaotropic solvent was confirmed, and as a result, it could be confirmed that the detection amount of Aβ 1-40 increased in all cases where the chaotropic solvent was used, and among them, the detection amount of Aβ 1-40 increased in the case where 2 M to 3 M of potassium thiocyanate was used and in the case where 6 M of guanidine hydrochloride was used (FIG. 20).

Example 9: Analysis of Alzheimer's Disease Onset Marker According to Chaotropic Solvent by Polyacrylamide Gel Electrophoresis For CAST GEL, an acrylamide content was determined according to the molecular weight of Alzheimer's disease onset markers. 15% Tris-glycine polyacrylamide gel was prepared with reference to the molecular weight of about 4 kDa in Aβ 1-40 and Aβ 1-42, and the molecular weight of about 36.8 to 45.9 kDa according to the isoform in T protein. 15% Tris-glycine polyacrylamide gel was prepared by mixing 2.3 ml of sterilized water, 5.0 ml of 30% acrylamide mix, 2.5 ml of 1.5 M Tris buffer (pH 8.8), 0.1 ml of 10% ammonium persulfate, and 0.004 ml of TEMED. A stacking gel was prepared by mixing 2.7 ml of sterilized water, 0.67 ml of 30% acrylamide mix, 0.5 ml of 1.0 M Tris buffer (pH 6.8), 0.04 ml of 10% ammonium persulfate, and 0.004 ml of TEMED. The prepared gel solutions were put sequentially in a gel caster and casted. While the gel was solidified, a 10× Tris-glycine buffer was diluted, and the sample and a protein weight standard marker were prepared. Here, if dilution of the sample was necessary, 1× Tris-glycine buffer was used. When the gel preparation was completed, the standard marker was put on the first line, the samples were set on the other lines and loaded at 20V for about 10 hours. Then, a stacking gel portion was cut off and removed from the polyacrylamide gel, and the loaded protein was stained by immersion with 50 ml of 10 times diluted brilliant blue G solution. Here, the protein was stained for 13 hours while shaking at 50 rpm on an orbital shaker, and rinsed with sterilized water until bands were visible after staining.

Meanwhile, ammonium bicarbonate (ABC) was dissolved in water to prepare a 25 mM aqueous solution. Then, guanidine hydrochloride, guanidine thiocyanate, and potassium thiocyanate were dissolved in the 25 mM ammonium bicarbonate (ABC) aqueous solution prepared above to prepare a 20 M stock solution. The stock solution was used to prepare a sample, followed by electrophoresis.

Example 10. Confirmation of Nanoplasmonic Biosensor in AD Patient Sample

We confirmed the medical usefulness of this nanoplasmonic biosensor that was assisted by a chaotrope for the diagnosis of AD from the blood samples of patients (FIG. 22). We also proved that this highly sensitive platform distinguishes between normal control and AD patients. The plasma samples were obtained from pooled normal human plasma and AD human plasma (Innovative Research Inc., Novi, Mich.). The patients had been clinically diagnosed as AD, and this status continues (mean age: 72.6±6.3; 3 women, 2 men). We measured the Rayleigh scattering shifts of τ protein-specific immunogold before/after the injection of cognitive normal control plasma and the patients' samples (Patient No. 1-5), with or without 6 M Gua-HCl. The concentration of τ protein in blood is high in patients with Alzheimer's disease.10,18,19 In cases 1, 4 and 5, the LSPR $\lambda_{max}$ shift values were lower than that of the control when the chaotrope was not used (Black bars in FIG. 22). The assay without the chaotrope did not discriminate between AD and control patients. In contrast, the combination of the plasmon biosensor and the chaotrope resulted in the assays of patients having a higher LSPR $\lambda_{max}$ shift than those of controls with the chaotrope (Grey bars in FIG. 22). The chaotrope partly disassembled aggregated τ proteins in blood 41 and uncovered the τ protein epitope from blood proteins. The biosensor could therefore react with all of the τ protein in blood, and its accuracy and sensitivity for the diagnosis of AD was enhanced with 6 M Gua-HCl. Plasma τ protein levels were significantly higher in subjects with AD than controls. The average Rayleigh scattering peak shifts were 8.96±0.93 nm after the injection of AD plasma with 6 M Gua-HCl and 5.9±1.07 nm for controls with the chaotrope (FIG. 22). This finding was supported by studies that showed that τ protein concentrations in plasma samples increased in the order from subjects with normal control and mild cognitive impairment (MCI) to AD and early-stage AD patients.15,18,23 Additionally, AD plasma τ protein levels were negatively associated with the most valuable imaging diagnosis factors, including total hippocampus volume and the grey matter density of the superior frontal gyrus.47,48 Other regression analyses as well as the identified negative association of cognitive functions and plasma T protein levels have been proven to correlate to delayed recall of logical memory and verbal fluency.18 On the other hand, the two Aβ isoforms did not differentiate between AD and control patients even though we demonstrated the high sensitivity of a nanoplasmonic biosensor with chaotropes. Recent studies have also shown that plasma Aβ and 42 levels are similar in AD and control groups. These findings sustain the idea that only plasma τ protein can provide insights regarding this pathological process in brain. Our proposed system is an optimized clinical assay to accurately diagnose AD patients by the precise detection of τ protein in plasma and reducing the overlapping range between concentrations

TABLE 9

| Blood | 10 µl | 5 µl | 5 µl | 5 µl | 5 µl | 5 µl | 5 µl | 5 µl | 5 µl |
|---|---|---|---|---|---|---|---|---|---|
| Dibluting Solution (Tris-glycine buffer) | — | 47.5 µl | 4.5 µl | 4 µl | 3.5 µl | 3 µl | 2.5 µl | 2 µl | 1 µl |
| chaotropic solvent (20M) | — | 0.25 µl | 0.5 µl | 1 µl | 1.5 µl | 2 µl | 2.5 µl | 3 µl | 4 µl |
| final concentration | 0 | 0.5 | 1 | 2 | 3 | 4 | 5 | 6 | 8 | of the protein in an age-matched control and AD patients' blood that presented a problem in prior studies. This combined use of a nanoplasmonic biosensor and a chaotropic agent provides a precise medical investigational method to determine the core pathophysiology of AD in blood and to distinguish AD patients with high accuracy.

The method for diagnosing Alzheimer's disease according to the present invention is able to diagnose Alzheimer's disease by using blood that is easily obtainable from the human body, and thus it is possible to perform objective analysis without requiring a complicated surgical procedure for diagnosing Alzheimer's disease. Further, by applying the gold nanoparticles having various sizes and shapes, it is possible to confirm multiple onset markers on a single platform to thereby achieve multiple detection, and by pretreatment of the chaotropic solvent in order to compensate for the decrease in detectability caused when the onset marker present in blood binds to other proteins, it is possible to improve sensitivity of the diagnosis.

The present invention has been described in detail based on particular features thereof, and it is obvious to those skilled in the art that these specific technologies are merely preferable embodiments and thus the scope of the present invention is not limited to the embodiments. Therefore, the substantial scope of the present invention is defined by the accompanying claims and equivalent thereof.

The invention claimed is:

1. A method for diagnosing Alzheimer's disease in a subject suffering the same comprising the steps of:
   (A) pretreating a blood sample from the subject with a solution comprising a chaotropic solvent comprising 6M guanidine hydrochloride;
   (B) contacting the pretreated blood sample with a plasmonic sensor based on a plurality of gold nanoparticles to which T protein antibody is immobilized;
   (C) measuring a light scattering spectrum of the blood sample upon contacting with the plasmonic sensor; and
   (D) determining whether the Alzheimer's disease occurs in response to analysis of maximum wavelength mobility($\Delta\lambda$max) obtained from the light scattering spectrum.

* * * * *